(12) United States Patent
Carey

(10) Patent No.: US 7,491,709 B2
(45) Date of Patent: Feb. 17, 2009

(54) TREATMENT WITH HYALURONIC ACID

(76) Inventor: Wayne Carey, 1305 Redpath Crescent, Montreal, Quebec (CA) H3G 1A1

( * ) Notice: Subject to any disclaimer, the term of this patent is extended or adjusted under 35 U.S.C. 154(b) by 105 days.

(21) Appl. No.: 11/477,532

(22) Filed: Jun. 30, 2006

(65) Prior Publication Data

US 2007/0003505 A1    Jan. 4, 2007

Related U.S. Application Data

(60) Provisional application No. 60/695,446, filed on Jul. 1, 2005.

(51) Int. Cl.
*A61K 31/70*    (2006.01)
*A01N 43/04*    (2006.01)

(52) U.S. Cl. .............................. 514/54; 514/23; 514/60

(58) Field of Classification Search .................. None
See application file for complete search history.

(56) References Cited

OTHER PUBLICATIONS

Bergeret-Galley et al. Aesth. Plast. Surg. (2001), vol. 25, pp. 249-255.*
Duncan Aesthetic Surgery Journal (2004), pp. 574-579.*
Rubin Aesthetic Surgery Journal (2004), vol. 24, pp. 489-493.*

* cited by examiner

*Primary Examiner*—Patrick T Lewis
(74) *Attorney, Agent, or Firm*—Arent Fox LLP

(57) ABSTRACT

The present invention relates, generally, to methods of providing long-term minimization of wrinkles or folds in the skin by injecting a bolus of hyaluronic acid deep into the skin. The methods of the present invention are particularly beneficial for improving the contours of the cheeks, filling folds under the eyes, and providing the visual effect of a chin implant, without requiring the use of surgical procedures.

11 Claims, 4 Drawing Sheets

TREATMENT WITH HYALURONIC ACID

This application claims benefit of priority to U.S. Provisional Patent Application Ser. No. 60/695,446, filed Jul. 1, 2005, the contents of which are hereby incorporated by reference.

FIELD OF THE INVENTION

The present invention relates to novel methods of treatment using hyaluronic acid. More particularly, the invention relates to methods of correcting tissue prolapse and/or tissue atrophy (or loss) by administering injections into the deep part of the skin (i.e., deep fat or just above the bone) using large injections of hyaluronic acid which has been formulated for injection into the superficial part of the skin.

BACKGROUND OF THE INVENTION

Hyaluronic acid, which is also referred to as hyaluronan or "HA," is a naturally occurring, water soluble polysaccharide that is a major component of the extracellular matrix and is widely distributed in animal tissues. Naturally-occurring HA generally has a molecular weight range of between about $6 \times 10^4$ to about $8 \times 10^6$ Daltons. It has excellent biocompatibility and does not produce a foreign body or allergic reaction when implanted into a subject.

Methods of preparing commercially available hyaluronan are known. Further, many forms of HA have been employed, for example as surgical aids to prevent post operative adhesions of tissues, as adjuncts to synovial fluid in joints, as fluid replacement and/or surgical aids in ophthalmic surgery, as a scaffold for tissue engineering in vitro or guided tissue regeneration or augmentation in vivo, and the like.

Hyaluronic acid (HA) gel products have been injected into joints for arthritis and superficially into the skin to treat wrinkles. In the skin they are typically injected as tiny drops or feathered into the skin as fine lines in the layer called the dermis. The skin is divided into the epidermis the most outer layer and then the dermis and then the fat and lastly the muscle and or bone. If one injects into the fat using the above techniques with the available commercial products, it is expected that the material will disappear quickly because the body breaks down the material with a naturally occurring enzyme called hyaluronidase. HA that is deposited in the form of relatively small microdroplets or feathered lines can be readily broken down by hyaluronidase.

Previous attempts to inject a small amount of hyaluronic acid material along the ridge of the bone have been made, but they generally use a small amount of hyaluronic acid material to try to soften the appearance of grooves, such as those that commonly occur under the eyes.

Recently, in 2006, a deep form of HA treatment using a larger molecule of HA was approved in 2006 for injection into deep tissues using a large bore needle. However, this technique requires a surgical incision to permit entry of the needle. The longevity of this treatment is presently believed to be about 1 year.

Accordingly, none of the above-mentioned techniques provides long-term methods for minimizing the appearance of deep wrinkles or folds in the skin by administering bolus injections of hyaluronic acid. There is a need in the art for long-term, non-surgical methods that are useful for reducing or eliminating undesirable folds or wrinkles of the skin.

SUMMARY OF THE INVENTION

In the technique of the present invention, a relatively large amount of hyaluronic acid, for example an entire syringe, is emptied into one area without moving the needle, thereby creating a deep nodule or bolus of the hyaluronic acid material that does not break down readily. Without being limited by any particular mechanism of action, it is theorized that when this technique is employed, the breakdown of the HA is prevented because of limited access by the hyaluronidase, or because of the creation of an amorphous avascular mass which is walled off and therefore inaccessible to enzymes. This deep nodule or bolus of HA lifts up the skin.

The methods of the invention are useful for correcting tissue prolapse and/or tissue atrophy (or loss), particularly in the area of the upper middle face and cheek. The methods of the invention involve administering injections into the deep part of the skin (i.e., deep fat or just above the bone) using large injections of hyaluronic acid which has been formulated for injection into the superficial part of the skin. By defining certain important injection sites, the present inventor has been able to develop a technique which allows the cheek to be sculpted and permits the groove under the eye to be lifted, giving a more youthful appearance.

Embodiments of this invention include raising the cheek and lifting the groove under the eye to a higher location typically seen in a younger face. A unique feature of the present invention technique is the creation of the bolus, that is, creating a nodule in the deep tissue that can obliterate the groove and also raise the cheeks, while providing better durability and a long-lasting effect.

In a first embodiment of the invention, the bolus technique is used to form a nodule of hyaluronic acid in an imperfection in the skin of a patient. The imperfection may be a wrinkle, fold, scar, or sunken area.

In another embodiment of this invention, an injection can be made the same way into the tissue to create the effect of an implant. Preferred locations for such implants include the chin and the cheek. Creating such a nodule in the deeper tissue may also have applications in other areas of the body.

In a further embodiment of this invention, the bolus technique is utilized to repair what is referred to as malar bags or festoons, which are sacks of loose skin seen under the eyes, by filling the area under the bag with a nodule.

Other features and advantages of the present invention will become apparent to those skilled in the art upon examination of the following or upon learning by practice of the invention.

DETAILED DESCRIPTION OF THE DRAWINGS

DESCRIPTION OF THE PREFERRED EMBODIMENTS

The term "hyaluronic acid" (HA) as used in the present application refers to hyaluronic acid or salts of hyaluronic acid, such as the sodium, potassium, magnesium and calcium salts, among others. The term "hyaluronic acid" is also intended to include not only elemental hyaluronic acid, but hyaluronic acid with other trace of elements or in various compositions with other elements, as long as the chemical and physical properties of hyaluronic acid remain unchanged. In addition, the term "hyaluronic acid" as used in the present application is intended to include natural formulas, synthetic formulas or combination of these natural and synthetic formulas.

Embodiments of this invention are directed to a technique where a relatively large amount of hyaluronic acid, for example an entire syringe, is emptied into one area creating a deep nodule of the hyaluronic acid material in the deep tissue that does not break down readily, perhaps by limiting access to the hyaluronidase. The deep nodule or bolus lifts up the skin.

The methods of the invention may be beneficially used to correct tissue prolapse and/or tissue atrophy (or loss) in any area, and are particularly useful when applied in the area of the upper middle face and cheek. The methods of the invention involve administering injections into the deep part of the skin (i.e., deep fat or just above the bone) using large injections of a hyaluronic acid composition that has been formulated for injection into the superficial part of the skin. By defining certain important injection sites, the present inventor has been able to develop a technique which allows the cheek to be sculpted and also raises the groove under the eye giving a more youthful appearance.

Embodiments of this invention include raising the cheek and lifting the groove under the eye to a higher location, as is typically seen in a younger face. One unique feature of the Tri-Site Bolus™ technique of the present invention is the creation of the bolus, that is, creating a small nodule in the deep tissue that can obliterate the groove and also raise the cheeks and also have a longer durability. The nodule can be, for example, approximately the size of a grape. However, modification of the shape and size of the nodule to suit the particular application is envisioned in accordance with the present invention.

In another embodiment of this invention, an injection can be made the same way into the chin to create the effect of a chin implant. Such implants can also be created in other locations where a raised contour is desired, such as the cheekbones.

Creating the non-visible nodule in the deeper tissue may have applications for other areas. For example, the nodule may be formed in the fatty tissue of the cheek, in order to counter the hollow-cheeked appearance that commonly occurs as a result of aging.

Figure 1:
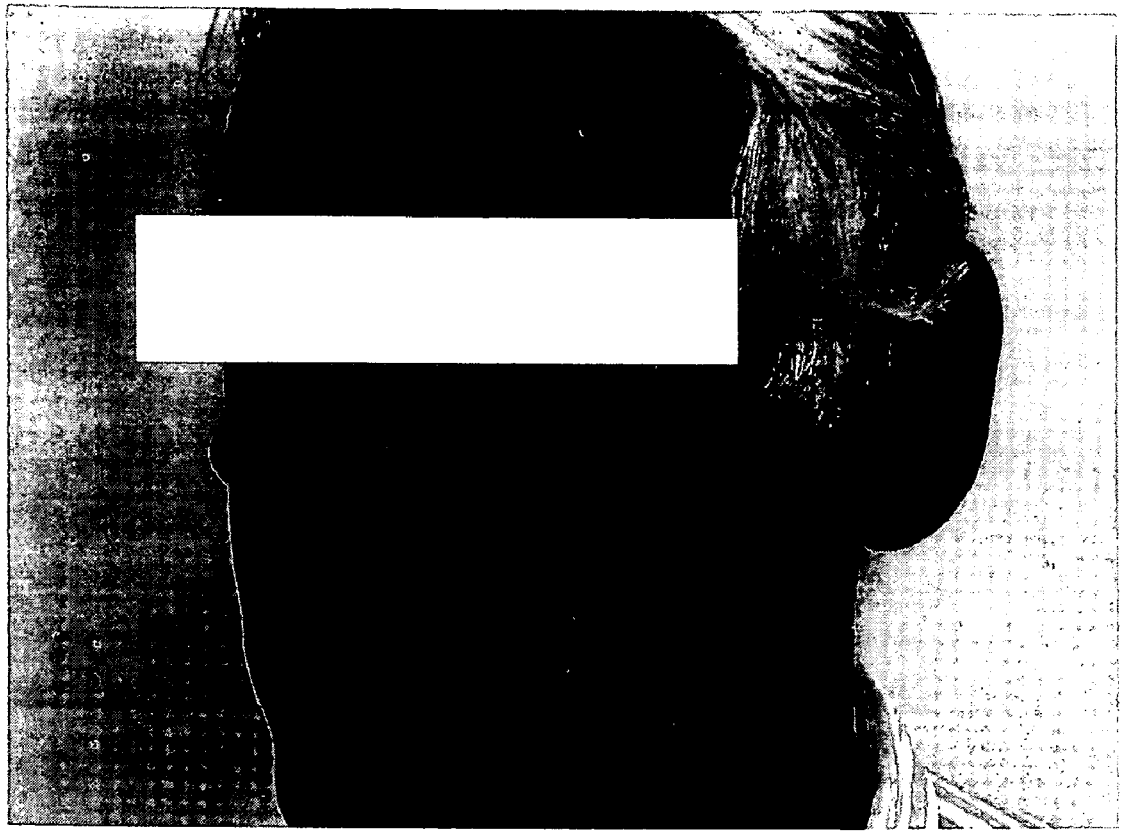
FIG. 1 is a photograph showing a side view of a prominent malar bag under a patient's left eye.
Figure 2:
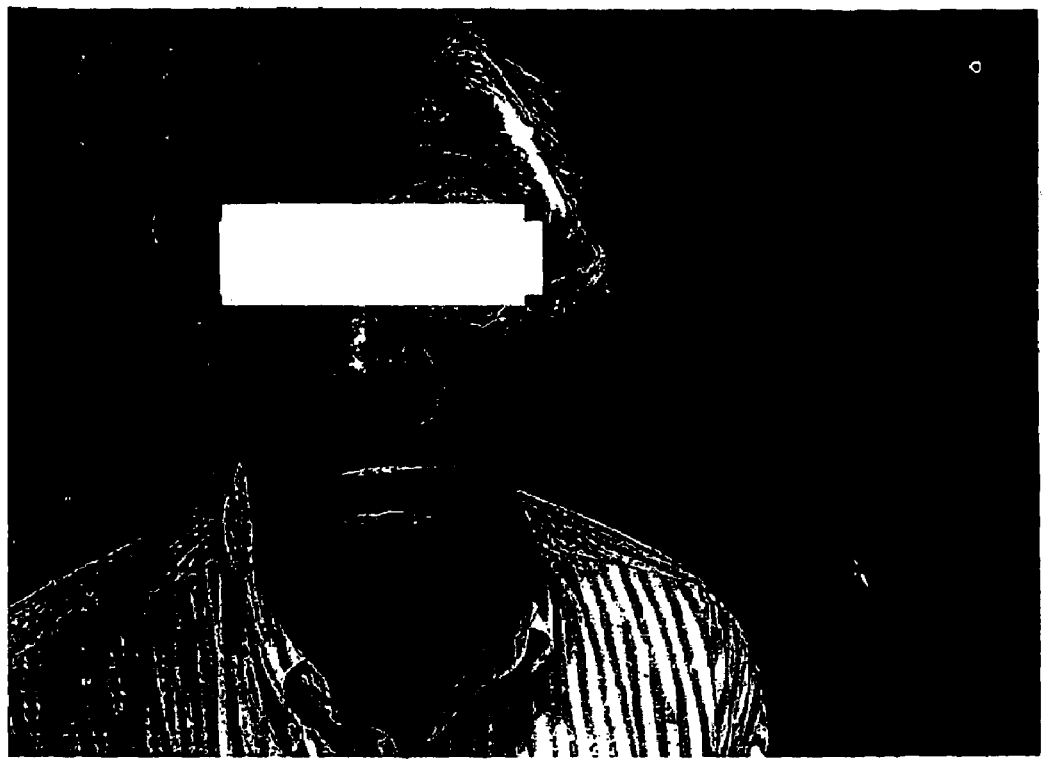
FIG. 2 is a photograph showing a front view of the prominent malar bag under the patient's left eye.
Figure 3:
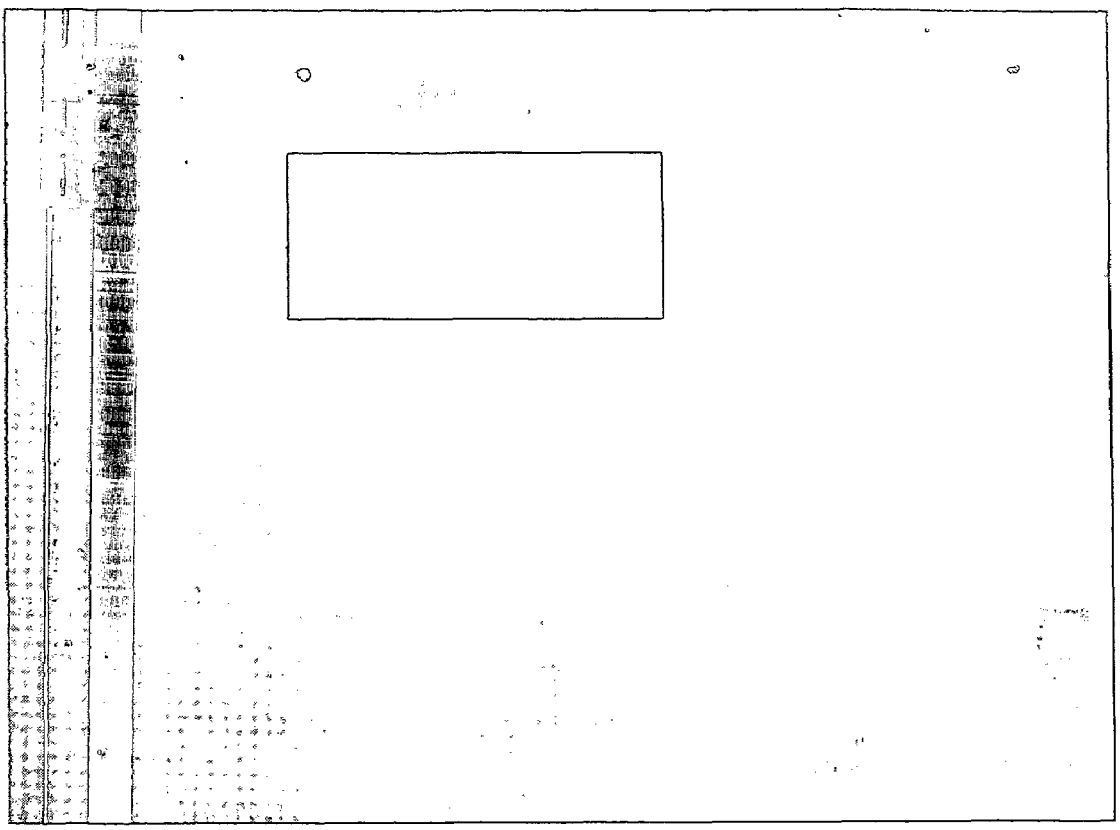
FIG. 3 is a photograph showing a showing a side view of the patient's left eye after being treated in accordance with the methods of the present invention.
Figure 4:
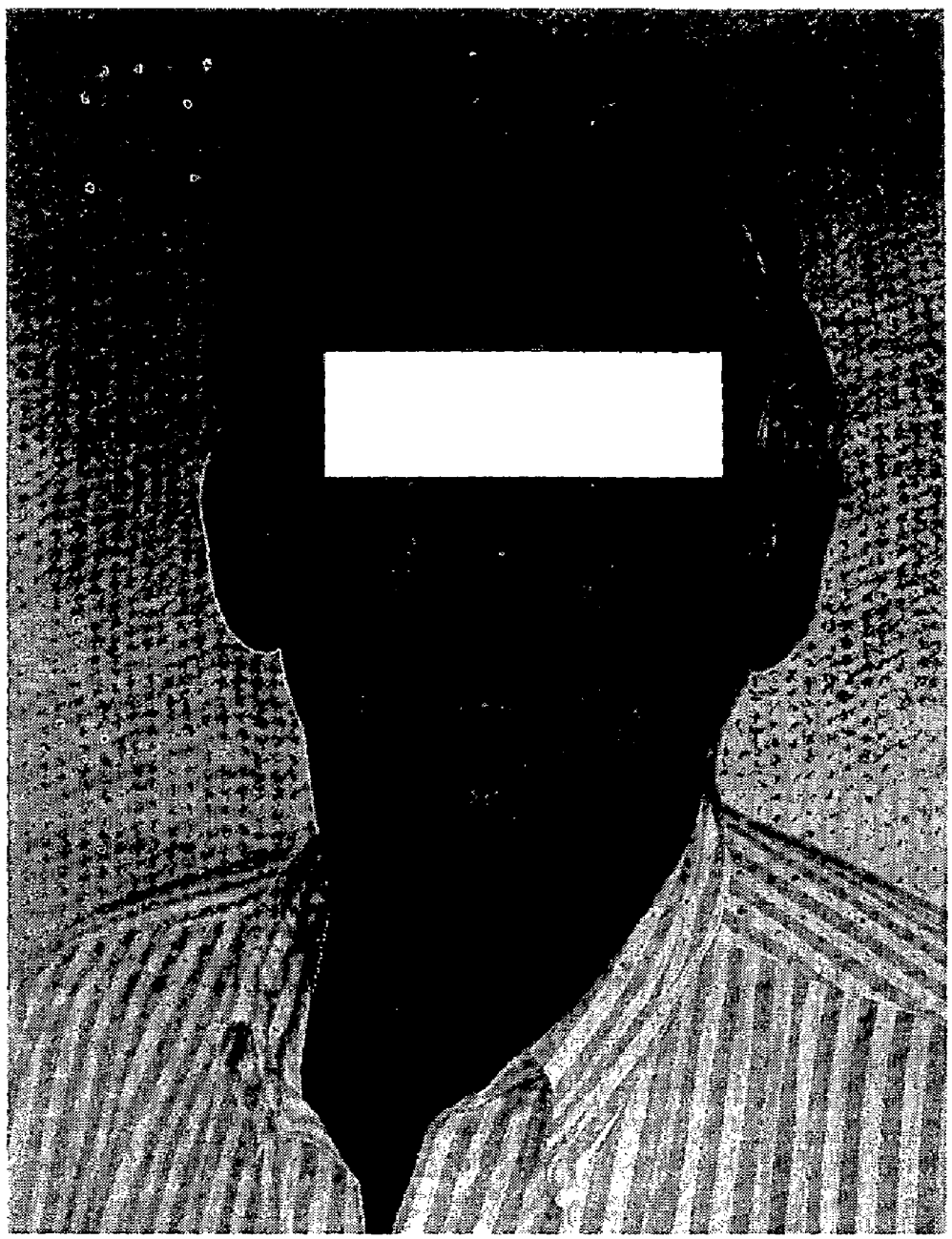
FIG. 4 is a photograph showing a front view of the patient's left eye after being treated in accordance with the methods of the present invention.

In another embodiment of this invention, the same bolus technique is utilized to repair what is referred to as malar bags, which are sacks of loose skin seen under the eyes. Typically, surgery cutting out the excess skin was the only option. FIGS. 1-4 are photos that show the correction of a prominent malar bag under the left eye of a patient using the methods of the present invention. Thus, the bolus technique can be effectively utilized for correction of malar bags using injections of hyaluronic acid.

The injections used in the methods of the present invention can be made, for example, at a depth of 0.3-1.5 cm below the surface of the skin. However, one of skill in the art will appreciate that the depth at with the injection is made will vary depending on the specific injection site. Further, the injections can be administered without requiring large bore needles or surgical incisions, as the methods of the present invention utilize small bore needles. Preferably, the hyaluronic acid bolus is injected into the skin using a needle having a gauge of from 24 (0.559 mm) to 30 (0.305 mm), where the bolus is more preferably injected using a needle having a gauge of from 26 (0.457 mm) to 28 (0.356 mm), and is most preferably injected using a 27 gauge needle (0.406 mm).

A hyaluronic acid product having a thickness of 30 viscosity is presently preferred. Examples of products that can be used include Juvederm® (a highly-crosslinked hyaluronic acid product sold by Allergan, Inc.) and RESTYLANE® Perlane® (a non-animal stabilized hyaluronic acid product used to fill deep folds, sold by Q-Med AB). For example, the product Juvederme® 30 can be effectively used in the embodiments of this invention. However, use of any medically-acceptable hyaluronic acid product is envisioned in accordance with the present invention.

In some embodiments of this invention, about 1.5 to 6, preferably about 3 to 4, full syringes (for example 0.7 cc or 0.8 cc syringes) can be injected on each side of the subject's face to fill wrinkles or folds in the skin. It is preferred that at least 1 cc, more preferably at least 2 cc, even more preferably about 2 to 3 cc, are injected on each side. One of skill in the art will appreciate that the amount of hyaluronic acid to be injected will also vary depending on the specific injection site.

Although the methods of the present invention primarily address the use of hyaluronic acid, use of other injectables is also envisioned. Additional uses for the methods of the present invention, beyond use in the cheeks, under the eyes, and in the chin, are also envisioned. For example, and without Limitation, the methods of the present invention may also be useful for filling scars or other surface deformities in the skin.

It will, of course, be appreciated that the above description has been given by way of example only and that modifications in detail may be made within the scope of the present invention.

The invention is capable of modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

What is claimed is:

1. A method for minimizing an imperfection in a patient's skin, comprising the steps of:
   injecting a bolus consisting of hyaluronic acid into deep fat underlying the dermis in an area affected by said imperfection;
   wherein said bolus of hyaluronic acid forms a nodule within the deep fat in the area affected by said imperfection.

2. The method of claim 1, wherein said nodule is formed within an imperfection selected from the group consisting of a wrinkle, a skin fold, a scar, atrophied skin, and sunken skin.

3. The method of claim 1, wherein said nodule is formed by injecting a bolus of from about 1 cc to about 3 cc of hyaluronic acid.

4. A method for reducing the appearance of a malar bag in a patient, comprising the steps of:
   injecting a bolus consisting of hyaluronic acid into deep fat underlying the dermis in an area below said malar bag;
   wherein said bolus of hyaluronic acid forms a nodule within the deep fat in the area below said malar bag.

5. The method of claim 4, wherein said nodule is formed by injecting a bolus of from about 1 cc to about 3 cc of hyaluronic acid.

6. A method for forming a non-surgical cosmetic implant in a patient, comprising the steps of:
   injecting a bolus consisting of hyaluronic acid into deep fat underlying in the dermis of a patient's skin;
   wherein said bolus of hyaluronic acid forms a nodule within the deep fat underlying the skin.

7. The method of claim 6, wherein said nodule is formed by injecting a bolus of from about 1 cc to about 3 cc of hyaluronic acid.

8. The method of claim 6, wherein said non-surgical cosmetic implant is a chin implant.

9. The method of claim 6, wherein said non-surgical cosmetic implant is a cheek implant.

10. The method of claim 9, wherein said cheek implant is provided in a lower portion of the cheek, in order to fill out a hollow cheek.

11. The method of claim 9, wherein said cheek implant is provided in an upper portion of the cheek, in order to raise an upper contour of said cheek.

* * * * *